United States Patent [19]

Stupka et al.

[11] Patent Number: 5,350,421
[45] Date of Patent: Sep. 27, 1994

[54] PROSTHETIC HEART VALVE

[75] Inventors: Jonathan C. Stupka; Jack C. Bokros; Michael R. Emken, all of Austin; Axel D. Haubold, Liberty Hill; T. Scott Peters, Georgetown, all of Tex.

[73] Assignee: ONX, Inc., Austin, Tex.

[21] Appl. No.: 958,049

[22] Filed: Oct. 6, 1992

Related U.S. Application Data

[63] Continuation-in-part of Ser. No. 837,761, Feb. 18, 1992, Pat. No. 5,192,309, which is a continuation-in-part of Ser. No. 674,871, Mar. 25, 1991, Pat. No. 5,152,785.

[51] Int. Cl.$^5$ .................. A61F 2/24; F16K 15/00; F16K 17/00; F16K 21/04
[52] U.S. Cl. ........................................ 623/2; 137/521; 137/527
[58] Field of Search ...................... 623/2; 137/521, 527

[56] References Cited

U.S. PATENT DOCUMENTS 5,078,738  1/1992  Covetil ................................. 623/2
5,108,425  4/1992  Hwang ................................. 623/2

Primary Examiner—Randall L. Green
Assistant Examiner—Dinh X. Nguyen
Attorney, Agent, or Firm—Fitch, Even, Tabin & Flannery

[57] ABSTRACT

Heart valves are shown which utilize pivot arrangements that create prompt response to flow reversal and minimize resistance to blood flow in the open position. Illustrated are valves having a pair of identical leaflets that can assume an orientation in the fully open position near maximum blood flow rate that is precisely parallel to the centerline of the passageway. The ability of the leaflets to assume a precisely parallel or low energy position in the bloodstream reduces pressure drop across the valve and results in improved flow characteristics. A camming action adjacent the upstream edges of the leaflets in combination with interengagement at downstream locations on the valve body, spaced from the locations where the camming action with said upstream edges occurs, positively guide the leaflets to assure effective closing movement regardless of momentary deviations in the dynamics of the reverse flow of blood through the valve. More particularly, slight closing movement pivoting, following assumption of such a parallel orientation, is effected by designing the interengagement so that the leaflets shift slightly downstream from the precisely parallel orientation when the blood flow slows prior to reversing and simultaneously rotate slightly toward their closed position orientation.

17 Claims, 6 Drawing Sheets

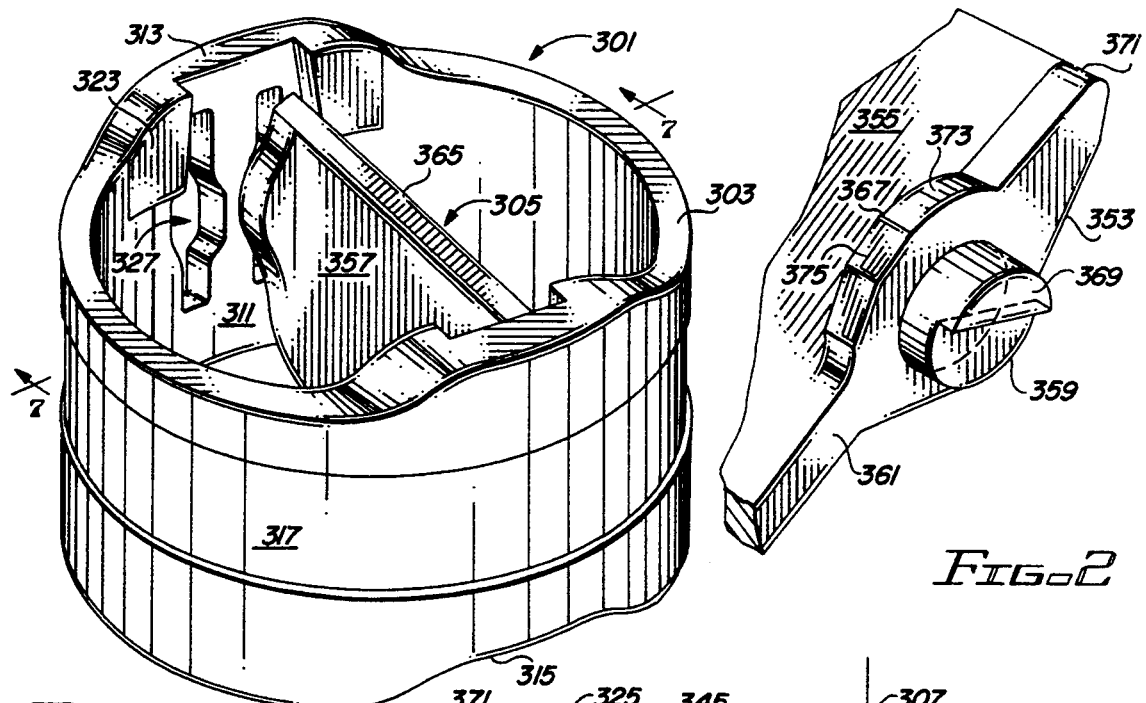
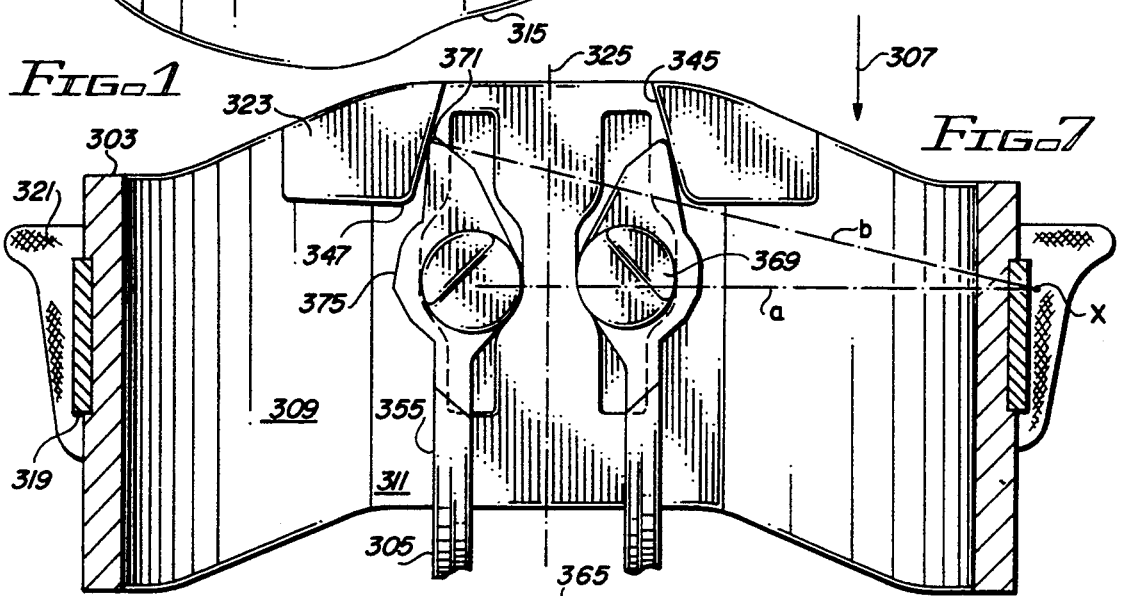
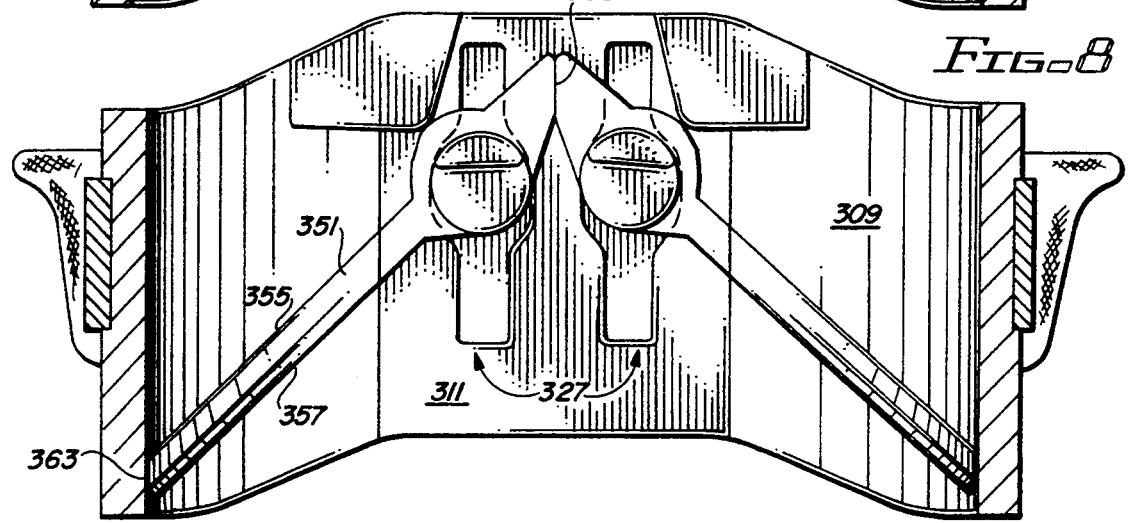

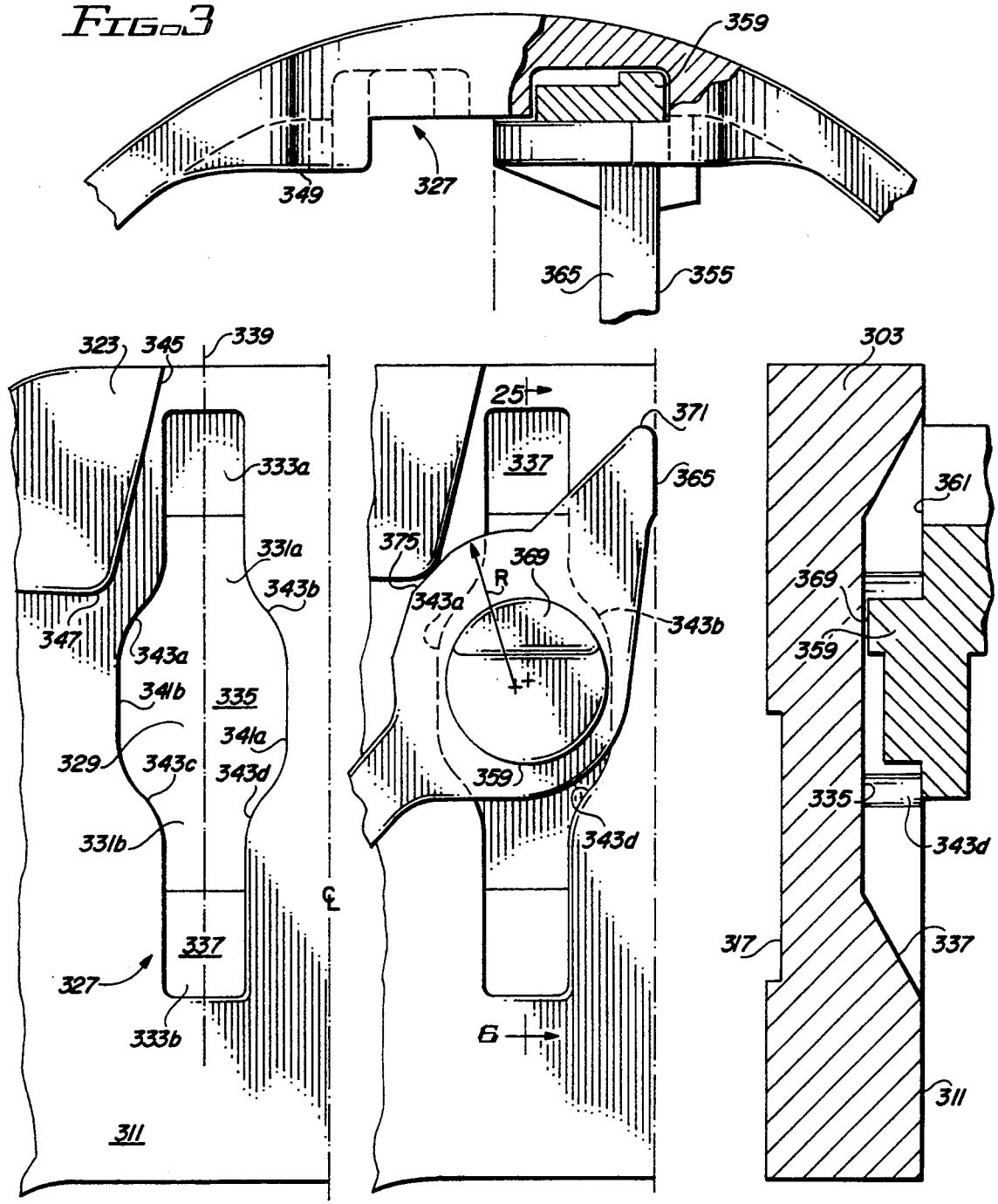

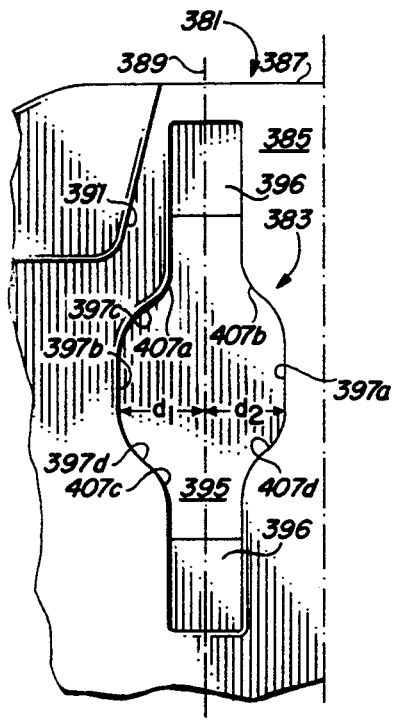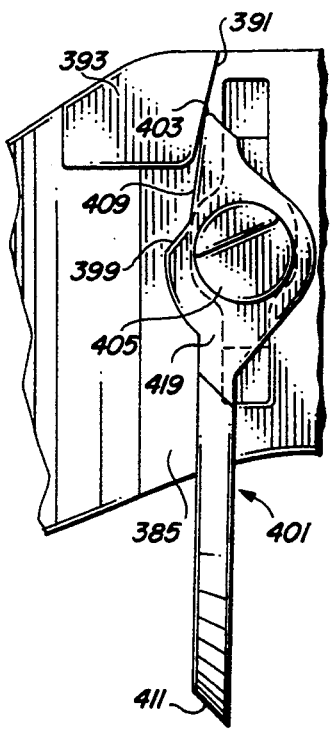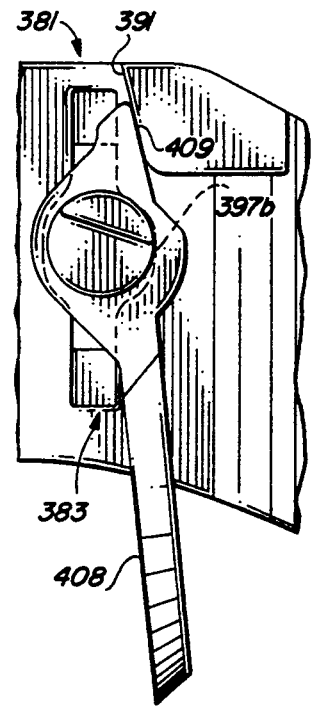
FIG.13　　　　　　FIG.15
FIG.14
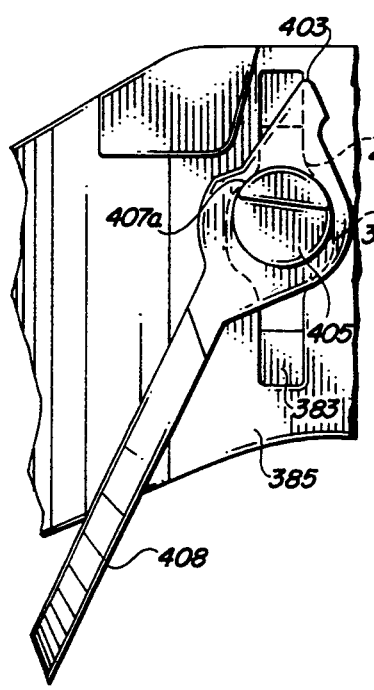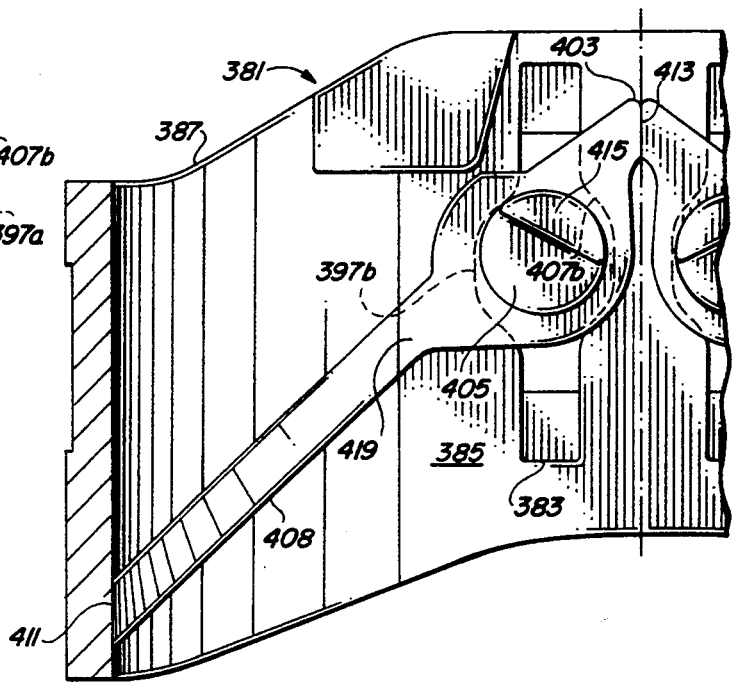
FIG.16　　　　　　FIG.17

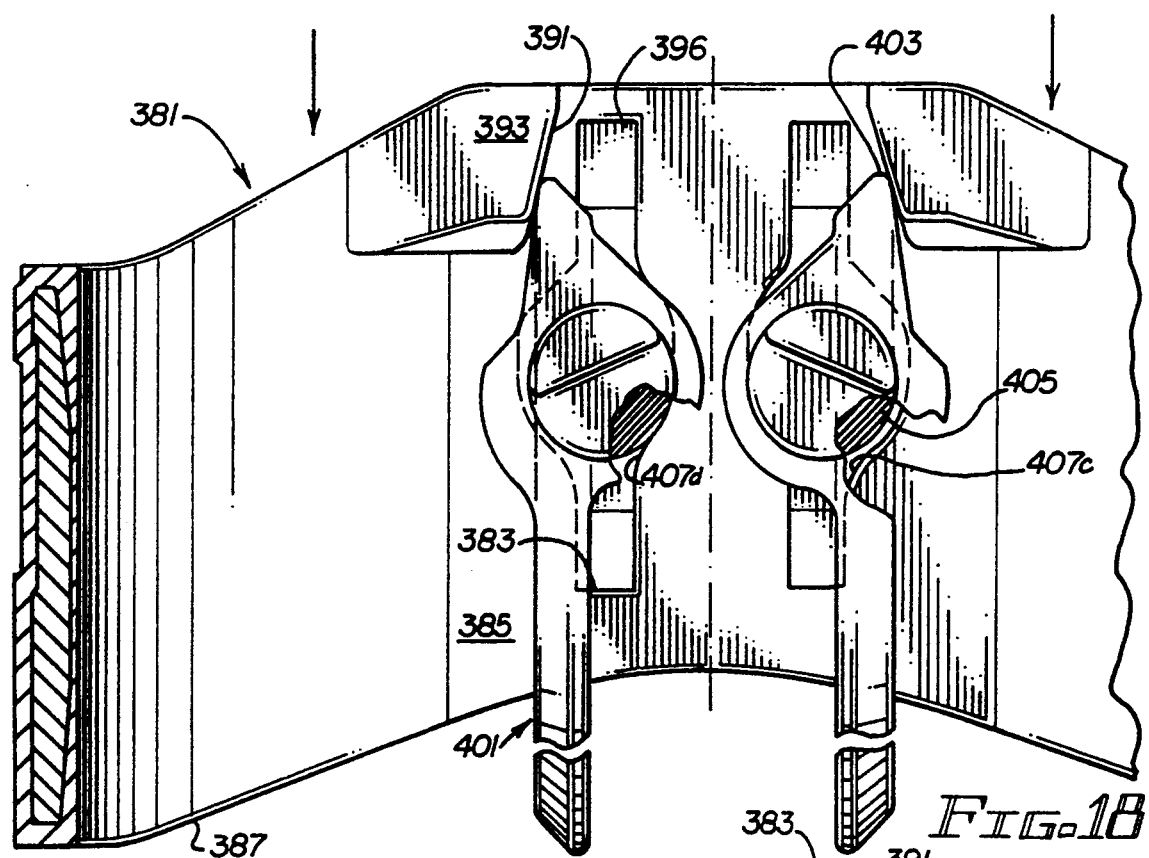
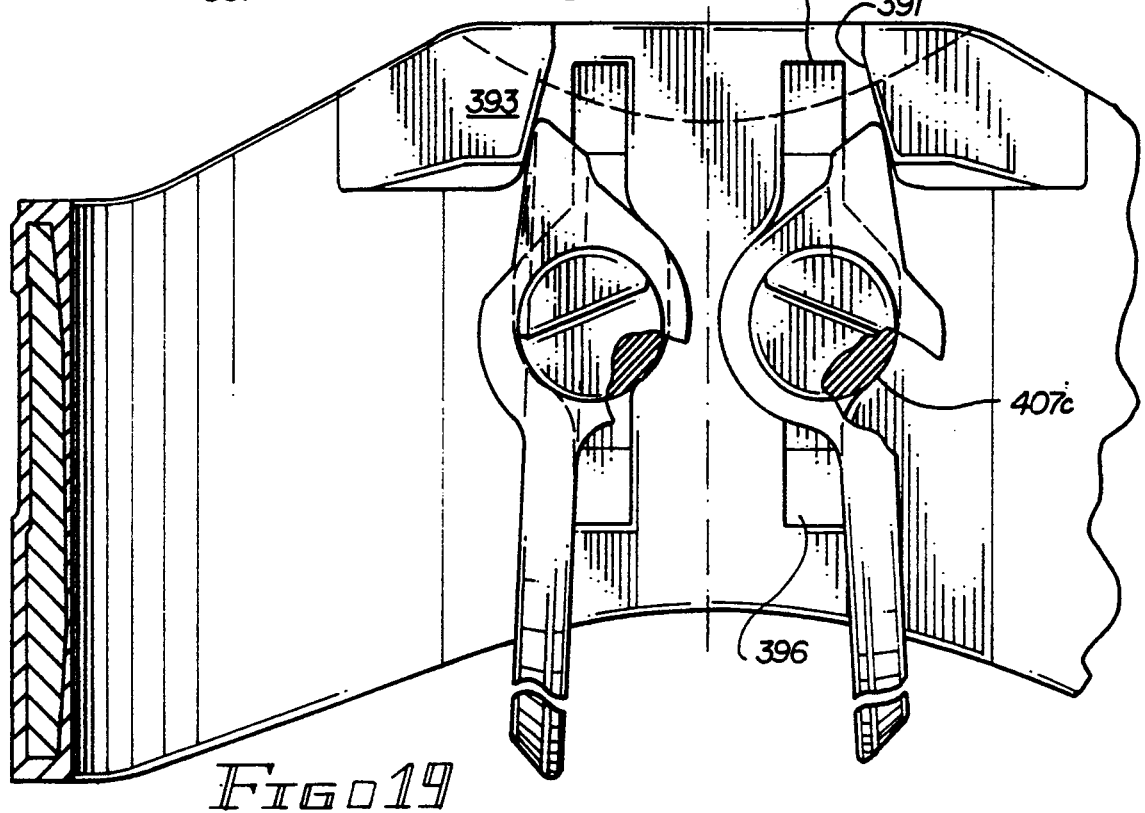

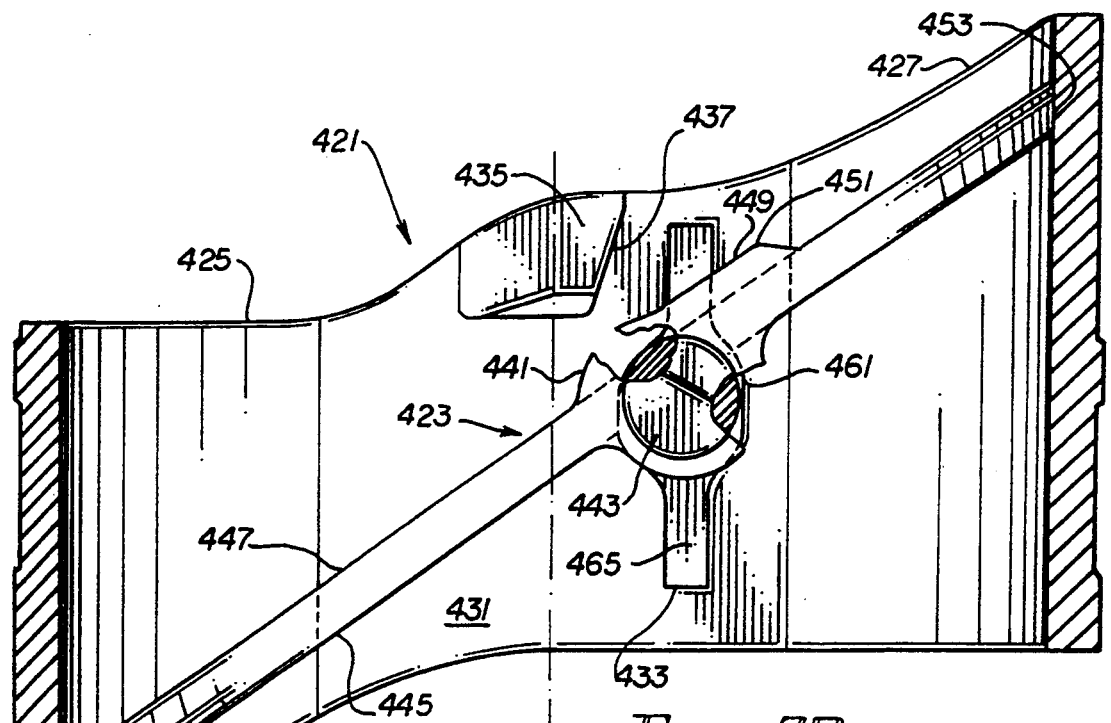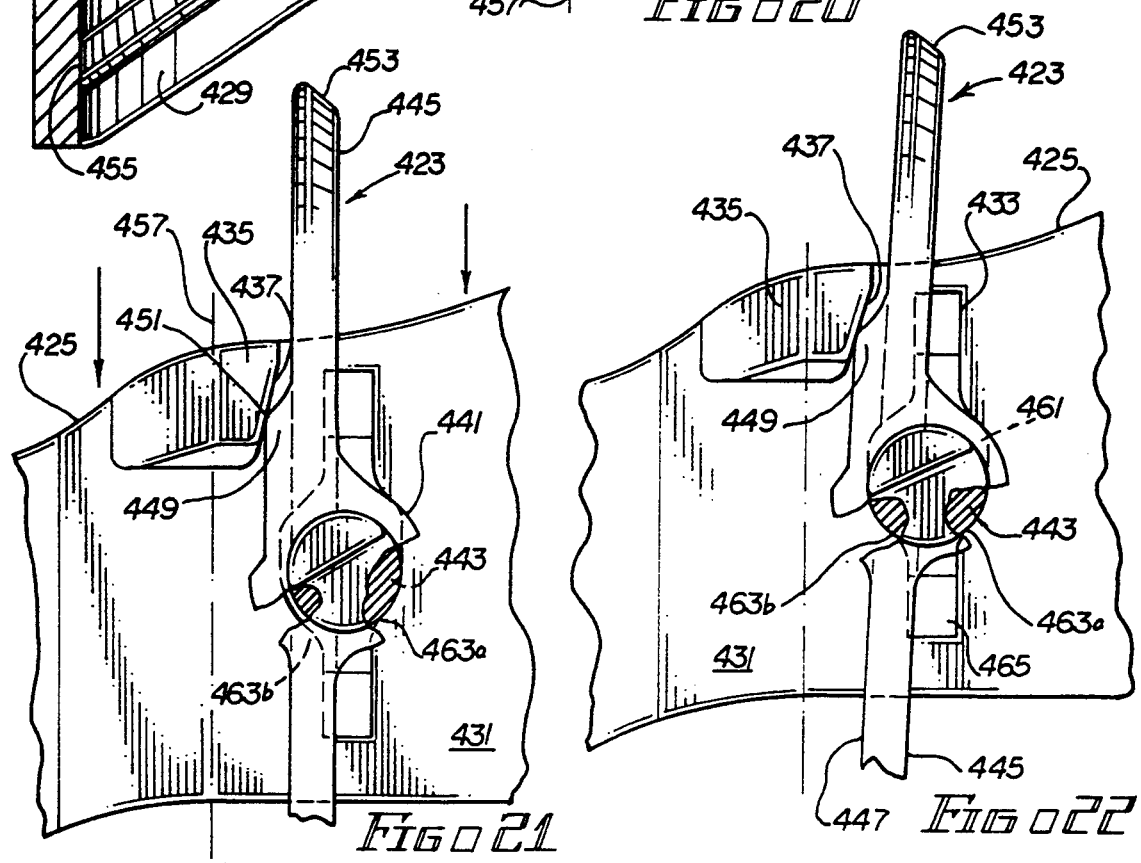

PROSTHETIC HEART VALVE

This application is a continuation-in-part of U.S. application Ser. No. 07/837,761, filed Feb. 18, 1992, now U.S. Pat. No. 5,192,309 which is continuation-in-part of U.S. application Ser. No. 07/674,871, filed Mar. 25, 1991, now U.S. Pat. No. 5,152,785.

FIELD OF THE INVENTION

The present invention relates to mechanical heart valve prostheses and, in particular, to improved prosthetic heart valves having valve members or occluders which both pivot and translate in moving between the open and closed positions.

BACKGROUND OF THE INVENTION

A wide variety of heart valve prostheses have been developed to operate hemodynamically, in conjunction with the pumping action of the heart, to take the place of defective natural valves. These valves are designed to function with valve members both in the form of a single occluder and a pair of occluders or leaflets, which valve members pivot along an eccentric axis (or both pivot and translate) to open and close a central blood flow passageway through the valve body.

U.S. Pat. No. 4,272,854 (Jun. 16, 1981) shows an early version of a bi-leaflet heart valve having an ear extending from each lateral side of the leaflet which pivots in a recess, guided in part by a knob which travels in a longitudinal slot that is cut more deeply into the sidewall of the valve body.

U.S. Pat. No. 4,373,216 (Feb. 15, 1983) discloses both single occluder and bi-leaflet heart valves wherein protrusions, extending radially inward from the flat sidewall sections of the valve body, guide valve members which have slots in their lateral edges to receive such protrusions.

U.S. Pat. No. 4,308,624 (Jan. 5, 1982) discloses heart valves of the single occluder and bi-leaflet type which have curved valve members which both rotate and translate in moving between the open and closed positions. Although the leaflets are intended to be able to assume a parallel orientation in the open position, as shown in FIG. 3, study of the arrangement shows that, upon reversal of blood flow through the passageway, the leaflets could translate upstream without beginning to rotate toward the closed position. Although pivoting could occur in the intended manner, once the leaflets have moved upstream guided by the path the spherical ears trace in the slots 21, one or both of the leaflets might possibly counterrotate, depending upon the instantaneous attitude of blood flow, and thereby not close on that stroke. U.S. Pat. No. 4,443,894 (Apr. 24, 1984) discloses a later version of this general type valve and illustrates an embodiment wherein the leaflets in their open position are angled relative to the centerline plane (see Column 4, lines 39–43) so that, when flow reversal occurs (as depicted in FIG. 4), the alignment of angled surfaces 44 of the stops 41 and their placement is such that there can be no inward pivoting or counterrotation of the leaflets (see Column 5, lines 34–41).

U.S. Pat. No. 4,451,937 (Jun. 5, 1984) shows additional single occluder and bi-leaflet valves wherein valve members, arranged at an angle to the centerline plane in the open position, pivot and translate to a closed position guided, in part, by laterally extending ears 21 which move in generally arcuate slots or depressions 23.

U.S. Pat. No. 4,328,592 shows other alternative embodiments of heart valves of this general type including some which have elongated slots in the valve sidewall with grooves to permit controlled leakage.

U.S. Pat. No. 4,692,165 (Sep. 8, 1987) discloses single occluder and bi-leaflet valves wherein valve members are guided in pivotal and translational movement in part by notches in their lateral edges which receive arcuate posts protruding from flat sidewall sections of the valve body.

U.S. Pat. No. 4,863,458 (Sep. 5, 1989) discloses bi-leaflet heart valves having leaflets of varying thickness which are guided in translational and pivotal movement by laterally extending ears that are received in recesses formed in the flat sidewall sections of the valve bodies.

Commercially developed heart valves using valve members of this type, as generally exemplified by the last 3 U.S. patents mentioned above, have employed valve members which are oriented at an angle to the centerline plane in the open position, so that the backflow of blood will preferentially impinge upon the outflow surfaces of each valve member and thus tend to initially impart a pivotal component to its movement toward closing. It is now felt to be particularly important that mechanical heart valve prostheses should provide passageways through which blood will flow freely with a minimum of drag in the open position and, to accomplish such end, that valve members should be able to assume an orientation which is parallel to the longitudinal axis of the passageway when the blood flow through the valve is at a high level; but, of course, these valves should also close quickly upon the occurrence of backflow to minimize regurgitation of blood. Improvements in construction to create mechanical valves having such characteristics have continued to be sought.

SUMMARY OF THE INVENTION

The present invention provides mechanical heart valve prostheses having the aforementioned desirable characteristics wherein a valve member or members can assume an open position parallel to the longitudinal axis of the valve passageway when blood flow is at its highest. However, to insure that such valve members will promptly begin to pivot toward the closed position orientation as soon as blood flow reversal, or backflow occurs at the valve, these valves are constructed so that additional downstream displacement of the valve member or members occurs as the velocity of the bloodstream slows, e.g., near the end of the pumping stroke, and as a result of this additional displacement, rotation occurs toward the closed orientation from this parallel orientation.

Illustrative valves include a pivot arrangement wherein a projection extends inward from the valve body interior wall and is located upstream of at least a portion of such valve member when it is in its open position. This projection is slidingly engaged by such valve member as soon as upstream displacement occurs upon blood flow reversal, creating a camming action that causes a positive pivoting moment to be applied to the valve member. Location of the projection so that such sliding, camming contact occurs at the upstream tip of the valve member maximizes the moment arm and further contributes to positive closing action.

To assure the desired positive closing action is effected, additional interengaging elements are also provided both on the valve body and on such valve member, at locations apart from where such camming contact occurs, which elements cooperate with such camming engagement and guarantee that the desired pivoting movement of such valve member continues throughout its desired path toward closure. These additional interengaging elements are in contact with each other at a first location on the valve body during the period of high bloodstream flow; however, downstream shifting occurs as the rate of blood flow decreases prior to reversing, as a result of which downstream shifting there is a slight rotation of such valve member toward its closed position orientation.

Illustrated are constructions wherein the interengaging elements comprise depressions or slots formed in the interior flat sidewall portions of the valve body wherein ears of generally right circular cylindrical shape are received. The slots have wider central sections flanked by narrower upstream and downstream sections which connect therewith. The transition region between the central section and the downstream section of the slot is defined by a pair of curved shoulders with a first curved shoulder defining the first, high blood flow position and with the two shoulders together defining the downstream contact position which the valve member assumes under reduced blood flow conditions.

BRIEF DESCRIPTION OF THE DRAWINGS

FIG. i is a perspective view of a bi-leaflet heart valve embodying various features of the present invention, shown with the left hand leaflet removed and with the right hand leaflet in the open position;

FIG. 2 is an enlarged fragmentary view, shown in perspective, of the leaflet from the heart valve of FIG. 1;

FIG. 3 is a fragmentary plan view partially in section of the bi-leaflet heart valve shown in FIG. 1 with the left hand leaflet removed and with the right hand leaflet shown in its open position;

FIG. 4 is an enlarged fragmentary view showing the elongated slot in the sidewall of the valve body and the adjacent projection;

FIG. 5 is a view similar to FIG. 4 showing the leaflet within the slot in the location where it would reside when the leaflets are both in the fully closed positions;

FIG. 6 is a sectional view taken generally along the line 6—6 of FIG. 5;

FIG. 7 is an enlarged cross sectional view of the heart valve, taken generally along the line of 7—7 of FIG. 1, showing both leaflets in elevation, installed and in the open position;

FIG. 8 is a cross sectional view similar to FIG. 7 showing the two leaflets in elevation and in the closed position;

FIG. 13 is a view, similar to FIG. 4, showing a fragment of an alternative embodiment of a heart valve body embodying various features of the invention, which has asymmetric slots provided in the interior sidewalls;

FIG. 14 is a view similar to FIG. 9 of a heart valve showing the left hand leaflet in the full open position in the valve body employing the asymmetric slots shown in FIG. 13;

FIGS. 15, 16 and 17 are views similar to FIGS. 10-12 showing a sequence of views as the leaflets translate upstream and rotate to their fully closed position upon reversal of blood flow through the valve having slots as shown in FIG. 13, with FIG. 15 showing the right hand leaflet;

FIG. 18 is a view similar to FIG. 14 showing both leaflets in the full open position as they would appear with high downstream blood flow through the valve in the direction of the arrows, with portions of the leaflets broken away so as to show the contact between the ears and the slot walls;

FIG. 19 is a view similar to FIG. 18 showing the leaflets after having moved to the ultimate downstream location during reduced flow conditions;

FIG. 20 is a alternative embodiment of a heart valve generally similar to the valve shown in FIGS. 13-19 but utilizing only a single valve member shown in the closed position, with the valve body being shown in section but with the valve member being shown in elevation with portions broken away;

FIG. 21 is a fragmentary view similar to FIG. 20 but showing the valve member in the full open position as it would appear during the highest rate of flow in the downstream direction of the arrows; and FIG. 22 is a view similar to FIG. 21 showing the valve member in its ultimate downstream position, having rotated slightly toward the closed position (from the FIG. 21 orientation) when conditions of reduced flow occur prior to reversal.

DETAILED DESCRIPTION OF THE PREFERRED EMBODIMENTS

Figure 9:
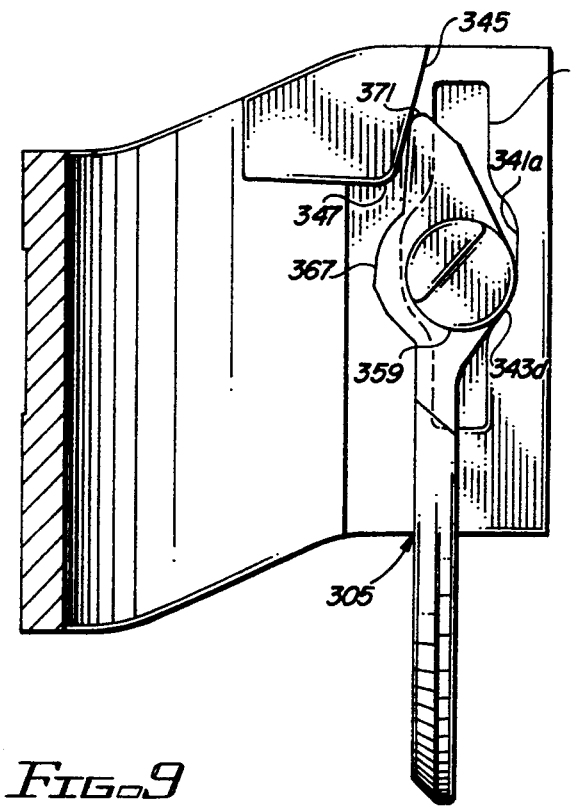
FIGS. 9, 10, 11 and 12 are fragmentary sectional views showing the left hand leaflet as it may move in translating and rotating from the fully open position (FIG. 9) to the fully closed position (FIG. 12)

Shown in FIGS. I to 12 of the drawings is a preferred embodiment of a prosthetic heart valve 301 constructed so as to embody various features of the present invention. The heart valve 301 is of a bi-leaflet construction; however, it should be understood that the principles of the present invention can be incorporated into a heart valve having a single valve member or occluder as generally shown and described in pending U.S. patent application Ser. No. 674,871, filed Mar. 25, 1991 now U.S. Pat. No. 5,152,785, the disclosure of which is incorporated herein by reference.

Very generally, these heart valves have improved flow characteristics, particularly when the valve is in the fully open position. Because the occluders can align substantially parallel to the valve centerline in the open position, or can align at slight deviations thereto depending upon local variations in blood flow path through the valve at any instant, they minimize drag and substantially reduce boundary layer separation along the major surfaces of the occluders. The valve design also provides good washing characteristics to prevent stagnation and potential clotting. Furthermore, heart valves of this design exhibit a rapid response to the change in direction of blood both in respect of opening and closing. Still further, in valves of this design, there is relatively low impact of the occluders against the valve body at the time of closing, thus reducing hemolysis or similar injury to blood cells and also eliminating potential problems with the creation of regions of substantial wear.

Heart valve 301 includes a generally annular valve body 303 which carries a pair of pivoting occluders or leaflets 305 that open and close to allow the flow of blood in the downstream direction as indicated by the arrow 307 in FIG. 7 and to prevent any substantial backflow of blood. The valve body 303 defines a blood flow passageway in the form of its generally cylindrical interior surface 309 which is interrupted by a pair of diametrically opposed flat wall sections 311. A pivot arrangement for defining the opening and closing movements of the leaflets 305 includes elements formed on the valve body 303 in the region of these flat wall sections 311, which elements coact with corresponding elements formed as a part of each of the leaflets.

The valve body 303 preferably has a scalloped design, and it is of relatively uniform longitudinal length along its entire circumference. Moreover, this length is preferably equal to at least about 45 percent, and more preferably at least about 60 percent, of the interior diameter of the passageway through the valve body. As best seen in FIGS. 1 and 7, the scalloping is such that the valve body 303 protrudes or bulges with upstream extensions 313 generally in the region of each flat wall section 311 and also has recesses 315 of substantially complementary shape along its downstream edge in the region of the flat wall sections, so as to maintain this preferred minimum length which is most preferably about constant around its entire circumference. The outer surface of the valve body is preferably formed with a shallow groove or channel 317 which receives a metal stiffening ring 319 that adds to the stability and rigidity of the valve body, which is otherwise preferably made of a material having some resiliency, such as pyrocarbon or pyrocarbon-coated graphite as well known in this art. Moreover, the stiffening ring 319 is used to support a sewing ring 321 of an appropriate design (see FIGS. 7 and 8) as is well known in this art. Examples of sewing or suture rings which could be employed are described in U.S. Pat. Nos. 4,535,483 and 3,691,567.

To create the pivot arrangement, the valve body 303 has four upstream projections 323 formed therein which protrude generally radially inward from the interior surface of the valve body and are arranged so that pairs of these projections generally flank the upstream ends of the two diametrically opposed flat wall sections 311 of the valve body. The passageway through the valve body is thus generally circular in cross section except for the two flat wall sections 311, and the centerline of this otherwise circular passageway is indicated by the reference numeral 325 in FIG. 7. An imaginary plane which includes the centerline 325 and which is perpendicular to the two flat wall sections 311 is referred to hereinafter as the centerline plane and is used for reference purposes throughout this specification and claims. In addition to the projections 323, the pivot arrangement includes a pair of depressions in the form of grooves or slots 327 formed in each of the flat wall sections 311 and arranged so that one lies on each side of the centerline plane. As best seen perhaps in FIG. 4, each of the slots has a central section 329 of constant width and constant depth and has upstream and downstream transition sections 331a and b, which narrow in width but remain of constant depth and which in turn lead to upstream and downstream terminal sections 333a and b. The width of the terminal sections 333 is between about 30 and about 60 percent of the width of the central section 329 and preferably between about 35 percent and about 50 percent. As best seen in FIG. 6, the base wall 335 of the slot central section 329 is flat and parallel to the flat wall sections 311 of the valve body interior sidewall. The flat base wall extends through the transition sections 331 of the slots, and then a pair of oblique walls 337 form the bases of the two terminal sections of each slot.

In this embodiment of the heart valve 301, the central section and the remainder of each slot 327 is formed symmetrically about a slot centerline which is indicated in FIG. 4 by the reference numeral 339. In another embodiment of the invention described hereinafter, the central sections of the slots are nonsymmetrical, being further offset from the centerline in a direction away from the centerline plane for a purpose to be explained hereinafter. The central sections 329 are formed with a pair of parallel flat sidewalls 341a and b which are preferably perpendicular to the base wall 335 and to the flat sidewall sections 311 of the valve body. In the transition sections 331, the slot sidewalls curve smoothly inward so as to narrow to the slot to a width equal to that of the terminal section, and these terminal sections are defined by curved wall sections which are indicated in FIG. 4 by the reference numerals 343a, b, c, and d.

The upstream projections 323, as best seen perhaps in FIGS. 3, 4 and 5, are each formed with a camming surface 345 which faces the centerline plane and is oriented at an angle of between about 5° and about 35° to the centerline plane, and preferably at an angle of between about 15° and about 30°. The downstream edge of this camming surface is rounded and preferably leads to an undersurface that is perpendicular to the centerline, although the undersurface itself is not functional. The interior surface 349 of each projection is also generally flat, as best seen in FIG. 3, and blends smoothly into the cylindrical sidewall 309 along its outer edge; however, if desired, it can be cut away along its upstream edge to provide a more streamlined flow of blood through the valve 301.

The leaflets 305 are preferably identical in shape and form; they have a generally flat main body section 351, preferably of substantially constant thickness, and have a pair of side sections 353 of greater thickness wherein the cooperating elements of the pivot arrangement are formed. Although the main body sections 351 of each leaflet are preferably flat, other configurations, such as cylindrical sections, can alternatively be employed as discussed in more detail in copending U.S. application Ser. No. 674,871, now U.S. Pat. No. 5,152,785. The flat main body sections of each leaflet are defined by an inflow surface 355 and an outflow surface 357 which are parallel to each other, and as best seen in FIG. 8, the inflow surface is the surface which faces upstream in the closed position whereas the outflow surface faces downstream. In addition to the thickened regions which constitute the side sections 353, each leaflet has a pair of arcuate ears or pegs 359 which extend laterally outward from the otherwise flat, lateral edge surfaces 361 of the side sections; the pegs 359 are received in the slots 327 and coact therewithin as a part of the pivot arrangement. The pegs are coaxial, and the axis is offset from the central plane through the flat leaflet body 351.

The leaflets 305 each have a major arcuate edge surface 363 which is located at the downstream edge of the leaflet in the open position and a minor mating edge surface 365 which is located at the opposite, upstream edge of the leaflet in the open position. The arcuate edge surface 363 preferably has a configuration such as to abut and seat against the cylindrical sidewall of the valve body in the closed position. The minor edge surface 365 is preferably flat and formed at an angle so as to mate flush against the corresponding mating edge surface of the opposing leaflet, as best seen in FIG. 8, and the minor edge surface is accordingly oriented at an angle to the main body section which is substantially the same as the downstream angle which the outflow surface 357 of the body section 351 of the leaflet forms with the centerline plane in the closed position, i.e. preferably an angle between about 30° to 60°. The angle in question defines the amount of angular rotation that each leaflet must undergo in moving from the fully open to the fully closed position inasmuch as the leaflets can assume the precisely parallel open position orientation. As a result, there may be advantages in having a smaller angle insofar as the leaflets need not rotate as great an angular distance in order to reach the fully closed position. Thus, this feature is taken into consideration in designing a valve, and in the illustrated embodiment, the angle is about 45°.

In addition to the major arcuate edge surface 363 and the minor mating edge surface 365, each leaflet includes a pair of the essentially flat lateral edge surfaces 361 which form the edges generally in the regions of the thicker side sections and from which the arcuate ears or pegs 359 protrude. These lateral edge surfaces 361 are preferably flat, and the leaflets 305 are proportioned so that there is minimal clearance between the flat wall sections 311 of the valve body and the flat lateral edge surfaces of the leaflets. This clearance is sufficient to enable the leaflets to freely pivot and to allow controlled leakage of blood through this slight gap when the leaflets are in the closed position, as generally known in this art. During pivoting movement, the lateral edge surfaces 361 will move closely adjacent the flat wall sections 311 of the valve body, one of which wall sections usually serves as a bearing surface for the pivoting leaflet.

The portions of the thickened side sections 353 of the leaflet that extend from the inflow surface 355 are formed with camming elements 367 which, as explained hereinafter, bear against the rounded downstream edges 347 of the projections and serve to define the closing movement of each of the leaflets. As best seen in FIGS. 2 and 7, the arcuate ears or pegs 359 which protrude laterally from the side sections 353 are preferably in the form of short right circular cylinders that are received within the central portions 329 of the slots and that have diameters such that there can be clearance along both edges as can be seen from FIG. 5. The diameter of such cylinders is preferably less than the axial length or height thereof, and the width of the central portion 329 of the slots 327 is preferably not more than about 10 percent greater than the diameter of the pegs 359. The outer ends of the pegs 359 are preferably reduced in size so that the outer end surface 369 of each peg has the shape of a sector of a circle. The purpose of this size reduction is to provide a controlled leak path that will assure the desired amount of cleansing flow in this region explained in more detail hereinafter.

The edge 371 of each leaflet at the upstream tip thereof, i.e. the junction between the minor mating edge 365 and the inflow surface 355, is rounded, and it constitutes the leading upstream edge of each leaflet in the closing movement thereof. It is this rounded edge 371 that coacts with the camming surfaces 345 on the pair of generally diametrically opposed projections 323, as explained in detail hereinafter, to initiate the closing pivoting movement of each leaflet.

The leaflets are installed in the valve body 303 by squeezing the body at diametrically opposite locations, as for example, along the reference line 7—7 of FIG. 1. The squeezing causes the diametrically opposed flat wall sections 311 to separate a sufficient distance farther from each other to allow the leaflets to be fitted into the interior passageway, with the laterally protruding pegs 359 being received in the respective slots. When the squeezing force is removed, the valve body 303 returns to its original annular configuration, leaving only the desired minimal clearance between the flat wall sections 311 of the valve body and the flat lateral edge surfaces 361 of the leaflets, in which position the leaflets are slidably-pivotally mounted for travel between the closed and open positions. The metal stabilizing ring 319 can be appropriately installed, as by shrink-fitting, following the installation of the leaflets; however, it may be preferred to install the metal stabilizing ring before installing the leaflets. The compressive force applied by the ring 319 can improve the structural properties of a pyrocarbon valve body, pyrocarbon being the preferred material of the construction, and the metal ring 319 has sufficient resiliency to return to its perfectly annular shape following removal of the squeezing force.

When the heart valve is installed in a patient, the two leaflets can assume the orientation illustrated in FIG. 7 wherein the major body portions 351 of both leaflets are precisely parallel to the centerline plane, assuming this is the "low energy" or equilibrium position; thus, they provide very low obstruction to the downstream flow of blood. Yet, despite such a precisely parallel open position, the present construction is such that closing movement of the leaflets begins immediately as flow reversal occurs. The leaflets are preferably mounted so as to, in the open position, divide the valve body passageway into three sections, a center section located between the two leaflets and two flanking sections, the cross sectional area of each of said flanking sections preferably being at least as large as the cross sectional area of said center section.

As best seen in FIGS. 7 and 9, when the leaflets are in the precisely parallel open position, the laterally extending pegs 359 are located at the downstream ends of the central portions 329 of the slots, and the rounded leading edge 371 of each leaflet is in contact with the camming surface 345 of the respective generally diametrically opposite projections. Depending upon tolerances, the actual contact between the right circular cylindrical surface of the peg 359 is with one or both of the curved sidewalls 343c,d that form the downstream transition section of the slot. In the embodiment illustrated in FIG. 9, the relative locations of the slots 327 and the projection camming surface 345 are such that contact occurs only between the surface of each peg and the curved sidewall 343d closer to the centerline plane.

Figure 10:
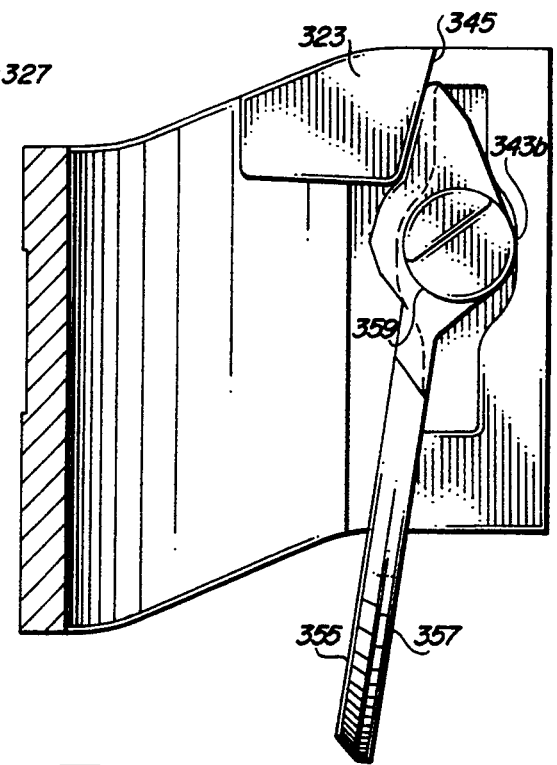

Upon the reversal of blood flow as a result of the contraction of the heart, the backflow of blood in an upstream direction (i.e. upward with respect to FIG. 7) displaces the leaflets upward. The path of their upward movement is defined by simultaneous engagement of the rounded leading edge 371 against the camming surfaces 345 and, at a substantial distance downstream therefrom, of the cylindrical pegs 359 against the flat sidewall 341a of the slot central portion, i.e. the sidewall closest to the centerline plane which faces away therefrom. As a result of the upstream edge being forced to follow this path of movement, the leaflet must begin to pivot or rotate from the parallel orientation shown in FIG. 9 toward its closed position, and comparison of FIGS. 9 and 10 shows that this left-hand leaflet has rotated clockwise as a result of its upward displacement. In this fully translated position, the inflow surface region of the side sections 353 lying just downstream from the leading rounded edge 371 lies in juxtaposition with the camming surface 345, and the right circular cylindrical surfaces of the pegs 359 each bear against the curved sidewall 343b of the upstream transition section of the slot.

Figure 11:
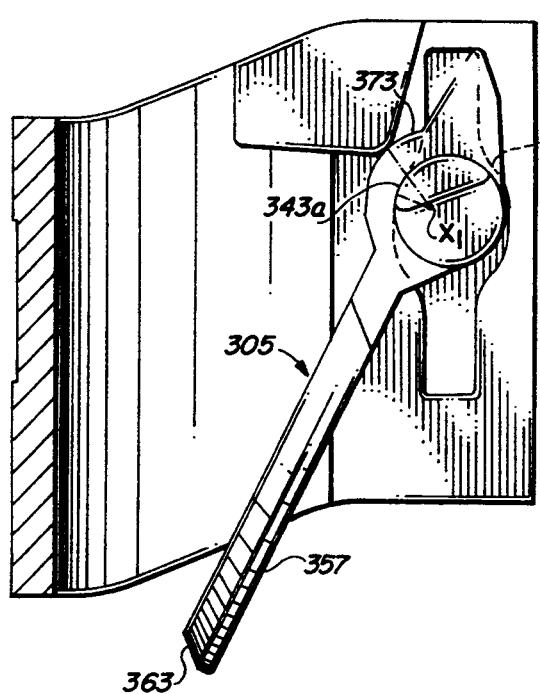

Because this prompt rotation has exposed the outflow surface 357 of the leaflet to more and more of the full force of the backflowing stream of blood, the rotative force vector being applied against each leaflet is amplified. Illustrated in FIG. 11 is a position where rotation has continued and the arcuate surface sections 373 of the camming elements 367 of both side sections are now in engagement with the rounded downstream edges 347 of the pair of projections. As a result, in the illustrated embodiment, the force of the flowing bloodstream has generally caused the cylindrical surface of the peg 359 to now bear against the curved sidewall 343a of the transition section and to lose contact with the curved wall section 343b closer to the centerline plane; however, this is subject to the dynamic conditions within the bloodstream at the moment. If external forces upon the patient or dynamic forces within the bloodstream are different, other intermediate positions could be reached.

Figure 12:
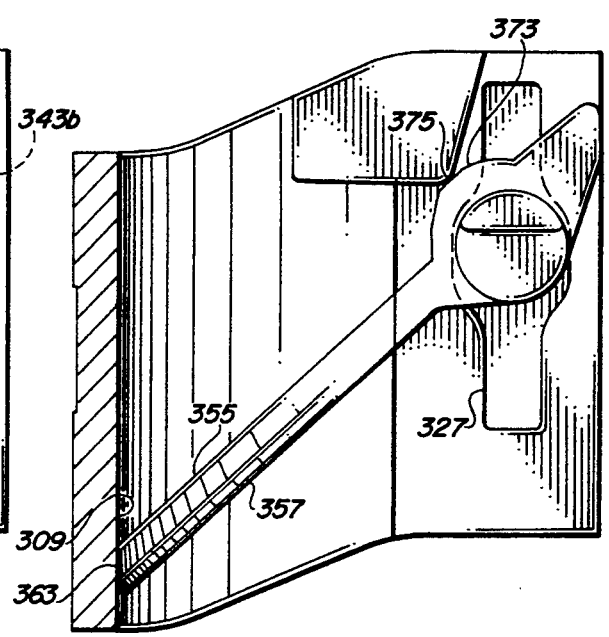

The last phase of the closing movement occurs when rotation has proceeded to the extent that a rear, flat camming section 375 (see FIG. 5) of each of the camming elements 367 of the side sections 353 has come into contact with the rounded downstream edges of the pair of projections. As best seen in FIG. 5, the radius of curvature R of the arcuate camming section 373 is offset slightly from the center of the right circular cylindrical peg 359 so that, as the rotation from the orientation generally shown in FIG. 10 occurs, the distance constantly increases from the center of the peg to the point on the surface of the camming element 367 in contact with the downstream edge of the projection so that contact with the curved sidewalls 343a of the slot is lost sometime as rotation continues, depending upon the dynamics of the bloodstream at the moment. The proportioning is such that, as shown in FIGS. 5 and 12, contact between the cylindrical surface of the peg 359 and the curved sidewall 343a that defines the upstream transition section must be lost before the major arcuate edge 363 seats against the interior cylindrical surface 309. Moreover, abutment of the two mating edge surfaces 365 of the leaflets assures that there is no contact between the surface of the peg 359 and the curved sidewall 343b closest to the centerline plane. As a result, this arrangement removes all of the load from the laterally extending pegs 359 at the moment of final closing movement which positively relieves potential wear in these regions and provides for a relatively soft closure. The length of the central sections 329 of the slots is preferably such that the straight line translation of the peg is not greater than a distance equal to about 50 percent of the diameter of the cylinder.

As been seen in FIGS. 3, 5 and 6, in the fully closed position, there is a controlled leakage path from the high pressure below (i.e. downstream of) the closed leaflets throughout the region of the pivot arrangement. More specifically, as can be seen in FIGS. 3 and 5, high pressure blood fills the lower portions of the slots 327, and controlled backflow is allowed along the straight sidewalls 341a, b of the central section 329 past the cylindrical surface of the pegs, which assures washing occurring at these locations. Moreover, as can be seen from FIGS. 3 and 6, the proportioning of the pegs is such that even when the lateral edge surface 361 of one of the leaflets is in contact with the respective flat sidewall section 311 of the valve body, there is a slight clearance between the base wall 335 of the slot and the edge surface 369 of the peg. Accordingly, there will also be a backflow of blood through this region. The amount of this backflow is controlled by adjusting the length of the flow path through the narrow region, as best seen in FIG. 6, by appropriately proportioning the reduction in size of the end of the peg 359 to either increase or decrease the area of end surface 369 which is in the form of the circular sector as best seen in FIGS. 2 and 5. In the illustrated embodiment, the leaflets, in the closed position, are oriented (i.e. have an angle of repose) at an angle of about 45° to the centerline plane; this angle is most preferably between about 40° and about 50°.

When the next pumping cycle of the heart occurs, so that there is again a flow of blood in the normal downstream direction through the valve 301, the force of blood on the inflow surfaces 355 of the leaflets causes their immediate displacement downward. Because of the eccentric axes upon which the leaflets 305 are mounted, there is also an immediate pivoting motion that occurs. The leaflets quickly reach the downstream transition region in the slots 327, and in this position, the cylindrical surfaces of the laterally extending pegs 359 bear against the curved sidewall surfaces 343c,d. Thereafter, essentially pure rotation occurs until the rounded leading edge 371 of the leaflet contacts the camming surface 345 of the projection, as shown in FIG. 9. This occurs an instant before the leaflet reaches its full open, i.e. parallel to the centerline, orientation, and the preferred location of the slot 327 is such that the leaflet is displaced just slightly toward the centerline plane so that the laterally extending pegs 359 are thereafter only in contact at about the Junction between the flat sidewall 341a of the central section of the slot and the curved sidewall 343d. This position is preferred because, with the pegs 359 in contact with the sidewall 341a of the slot nearest the centerline plane, upward displacement at the beginning of backflow immediately results in the beginning of pivoting motion as can be seen by comparing FIG. 10 with FIG. 9.

A particularly advantageous pivot arrangement is thus created by the deployment of projections which cause pivoting closing movement to begin as a result of contact with the rounded leading upstream edges 371 of the leaflets. When the closing movement first begins, there is a prompt and rapid rotation of the leaflets about a center of rotation of pivot (CRP) that is initially spaced a significant distance beyond the outflow surface 357 of the leaflet, preferably at least a distance equal to one-half the radius of the valve passageway. The term "CRP" is used to describe the theoretical instantaneous pivot center about which rotation of the leaflet is occurring at any instant in its movement from the open position to the closed position. Where there is contact with the valve body at two spaced apart locations generally along each lateral edge of the leaflet, i.e. (a) with the generally radially extending projections 323 and (b) with the sidewall of the slot 327, the CRP is determined by constructing perpendiculars to the respective supporting surfaces of the valve body at the precise points where such contact occurs and then determining the point where these perpendiculars cross. For example, assuming FIG. 7 illustrates the position of the leaflet as translation and rotation are just beginning, the CRP for the left hand leaflet would be at point X which lies at the intersection of the line (a) that is perpendicular to the flat sidewall 341a of the central section 329 of the slot and passes through the center or axis of the cylindrical peg 359 and the line (b) that is normal to the camming surface 345 at the point of its contact with the rounded leading edge 371 of the leaflet. These lines a and b and the intersection X are shown in FIG. 7. As a result, there is a very large initial effective torque which drives the leaflet in its rotational movement, achieving a prompt response to cause the leaflet to begin to move toward its closed position and minimizing the overall regurgitation of blood. Moreover, the location of the point of contact along the leading upstream edge of the leaflet increases the size of the moment arm which is contributing to the prompt initial opening movement of the leaflets.

In addition, a further significant advantage is found in this type of pivot construction because the CRP, during closing movement, shifts from its initial location (which as can be seen from FIG. 7, is not only well beyond the outflow surface 357 of the leaflet, but also beyond the centerline plane for the bi-leaflet valve) to a location near the outflow surface of the leaflet or even within the body of the leaflet when the leaflets near the end of their closing rotation. The change in location of the CRP during closing movement can be seen by examination of the embodiment illustrated in FIG. 11 where the point of intersection is labeled as the point $X_1$ and is located within the plane of the leaflet. As a result of this change in CRP location, there is a lessening of the rotational moment arm and a consequent softening of the final impact of the leaflet against the valve sidewall, thereby reducing both noise and wear.

The design is preferably such that there are two sets of force vectors supporting the leaflets in the fully closed position. One is at the points of contact between the interior cylindrical sidewall 309 of the valve body and the major arcuate edge 363 of the leaflet, and the other set is along the lines of contact between the rounded downstream edges 347 of the pair of projections and the respective rear flat sections 375 of the camming elements. The intersections of the composite vectors representative of these two sets of vectors when projected into a common plane parallel to the flat wall sections 311 can be adjusted as desired by adjusting the angle of the flat camming surface 375 in relationship to the plane of the inflow surface 355 of the leaflets. These considerations are explained in detail in copending patent application Ser. No. 674,871, now U.S. Pat. No. 5,152,785, and they are used to achieve the desired tight closing contact between the mating edge surfaces 365 of the leaflets which positively guards against undesired regurgitation leakage.

Overall, the illustrated embodiment, wherein there is contact between leading edge portions of each leaflet with the camming surfaces 345 of the projections along both lateral edges thereof and wherein there is also confinement of the laterally extending pegs 359 within the slots to thereby create coaction between the interengaging sidewalls of the slots 327 and the right circular cylindrical surfaces of the pegs, assures that precise control of the path of leaflet movement is maintained throughout the entire closing movement. The different dynamic conditions that occur within the bloodstream and that could potentially cause aberrations in occluder movement have more recently been taken into consideration in heart valve design, and it has been found that the combinations of interengaging elements illustrated in this patent application are particularly effective in assuring that the desired closing will occur regardless of such momentary aberrations.

Illustrated in FIGS. 13 through 19 are fragmentary views of an alternative prosthetic heart valve 381 also embodying various features of the invention. Inasmuch as there are substantial similarities between the valve 381 and heart valve 301 previously described in detail, the description of this alternative embodiment will concentrate on the differences between the two valves, and it should be understood that any features not specifically mentioned are essentially similar. One difference between the two valves lies nit he fact that, in the valve 381, depressions or slots 383 are formed in flat sidewall sections 385 of a valve body 387 in a manner so as to be asymmetric about a slot axial centerline 389. The location of the asymmetric slots 383 relative to camming surfaces 391 of projections 393 is adjusted to achieve the desired pattern of contact described hereinafter. The central portion 395 of each slot is offset laterally from the axial centerline of the slot (which is defined by the aligned upstream and downstream terminal sections 396) so that the portion of the central portion on the side away from the valve body centerline plane is wider, as best seen in FIG. 13. In other words, the flat sidewall section 397b of the slot central portion, lying farther away from (and facing toward) the centerline plane of the valve body, is spaced distance $d_1$ from the centerline 389 of the slot; this is greater than distance $d_2$ representing the spacing of the other flat sidewall section 397a that lies closer to the centerline plane of the valve body. The width of each terminal section 396 is about 35% of the width of the central portion of the slot 383. The flat sidewall 397b is flanked by short, oblique, flat upstream and downstream sidewall sections 397c and 397d which are spaced therefrom by short arcuate sidewall sections. Although thickened arcuate elements 399 do appear on side sections of the leaflets 401, they are not used to cam against rounded downstream edge surfaces of the projections 393 in guiding the final stages of closing movement; instead, once rotation of the leaflet 401 progresses to the extent that the upstream rounded tips 403 are no longer in contact with the camming surfaces 391 of the projections, further closing movement is essentially guided by the interengagement between the cylindrical surfaces of the pair of laterally extending pegs 405 and the cooperating sidewall surfaces of the slots 383. The axes of the pegs 405 are coaxial for each leaflet, but they are offset from the central plane of the flat body of the leaflets, as in the case of the leaflets 305.

FIGS. 14 through 19 illustrate differences between the valve 381 and the valve 301; however, except for the precise location and the asymmetric shape of the slots 383, the valve body 387 is essentially the same as the valve body 303. The pairs of slots 383 are likewise located in diametrically opposed flat sections 385 of the interior surface of the valve body.

FIG. 14 shows the left hand leaflet in its fully open position. With the leaflets 401 in this position, the pivot arrangement is functionally about the same as that supporting the leaflets 305 in the heart valve 301. There is contact between the upper leading edge 403 of each leaflet and the respective camming surfaces 391 on the pair of generally radially inwardly extending protrusions 393, and there is also contact between the pegs 405 and the downstream portion of the slot sidewall 397a at the curved sidewall or shoulder 407d, which is one of the four sidewall sections 407a, b, c, d that constitute curved shoulders and define two transition sections as previously described. In this full open position, leading edges 403 contact the the camming surface 391, and pegs 405 contact the curved shoulder 407d but are spaced from the curved shoulder 407c, which as seen in FIG. 18, is located slightly downstream of the shoulder 407d. As can be seen from FIGS. 14 and 18, both leaflets have their main flat body sections parallel to the centerline of the valve in this position, and a high flow rate of blood, i.e. near the maximum downstream level through the valve, which will occur, for example, during the pumping stroke of the associated chamber of the heart, exerts substantially equal forces upon both the inflow and outflow surfaces of each leaflet and tends to keep the leaflets in this precisely parallel alignment.

When the downstream flow of blood slows prior to the beginning of the reverse flow cycle, the forces of the flowing bloodstream tending to orient the leaflets parallel lessen so that the drag of the bloodstream against all of the surfaces becomes predominant and tends to move the leaflets slightly farther downstream as permitted by the contour of the slots. The downstream position and orientation of the leaflets is illustrated in FIG. 19. In this position, the curved upstream leading edges 403 have slid slightly farther downstream along the camming surfaces 391, but remain in contact therewith. The pegs 405 have moved downstream so as to now also be in contact with the curved shoulders 407c, sliding slightly downstream along the curved shoulders 407d while remaining in contact therewith. As a result of this shifting to their ultimate downstream positions, the flat body portions of the leaflets are no longer parallel to the centerline, but they have rotated toward the closed position orientation, i.e. so they are now preferably at an angle to the centerline of about 2 to about 5 degrees. As a result, regurgitation (i.e. the volume of blood which passes upstream through a prosthetic heart valve prior to the valve members reaching the fully closed position) is still further reduced because (a) the leaflets, upon the beginning of backflow, need to pivot fewer angular degrees to reach the closed position by reason of the headstart these leaflets have, as compared to the valve 301, and (b) the backflowing blood immediately preferentially contacts the leaflet outflow surfaces (as opposed to the inflow surfaces) so that the promptness of this component of the overall closing moment is further increased.

More specifically, as the reverse flow of blood begins, the leaflets 401 translate upstream, with the pegs 405 of the leaflet moving from the downstream end of the central portion 395 of the slot toward the upstream end thereof. As in the case of the valve 301 described earlier, this causes a camming force to be applied at the upstream edges 403 of the leaflets, as a result of the rounded upstream edges bearing against the camming surfaces 391 of the pair of generally diametrically opposed, inwardly extending protrusions 393 coupled with the interengaging contact (at a downstream location a substantial distance therefrom) between the pegs 405 and the central sections 395 of the slots. This interaction assures that pivoting of each leaflet toward the closed position orientation begins promptly. Driven by the force of the backflow of blood against the outflow surface 408, the application of which is accelerated by earlier slight rotation of each leaflet 401 at the end of the pumping stroke, the pegs 405 translate quickly to the upstream ends of the central sections of the slots, where they likely contact the oblique sidewalls 397c, as shown with respect to the right hand leaflet in FIG. 15.

The thickened side sections 399 at the lateral edges of each leaflet are reduced in height relative to the arcuate sections 373 so that they do not engage the projections 393 during the closing movement. The upstream translation of each leaflet 401 is first arrested by engagement of the laterally extending pegs 405 against the oblique wall sections 397c of the slots 383, at which instant there may also be contact simultaneously with the flat sidewall 397b as generally shown in FIG. 15. Because the curved shoulder 407a is located slightly downstream of the curved shoulder 407b, it is physically not possible for the peg 405 to contact the curved shoulder 407b.

In FIG. 15, the valve is illustrated as showing the peg 405 having contact with the oblique sidewall 397c and also bearing against the flat sidewall 397b that is farther from the valve centerline. In this orientation, the upstream portions 409 of the inflow surfaces of the leaflet side sections 399 are generally in juxtaposition against the camming surfaces 391 of the projections. Thereafter, the further movement of the leaflets is essentially one of rotation, but again the dynamic forces within the bloodstream will determine what the precise bearing points for the pegs 405 will be at any instant, i.e. against which flat sidewall 397 the pegs will be in contact.

In the view illustrated in FIG. 16, the bloodstream conditions are such that the peg 405 has at least momentary bearing contact with the flat sidewall 397a of the central region closest to the centerline plane and also with the oblique sidewall section 397c. As can be seen, the further rotation of the leaflet has caused all contact to be lost between the leaflet 401 and the projection 393, so that the continuing closing movement is thereafter guided by the interengagement between the pegs 405 and the sidewalls of the slots 383. The proportions of the peg 405 are preferably such that, at the upstream end of the slot 383, the peg will always contact the oblique flat section 397c.

FIG. 17 shows the final, fully closed orientation of the valve 381 wherein the major arcuate edge 411 of the leaflet is in contact with the cylindrical interior sidewall of the valve body 387, and wherein the minor mating edge 413 is abutting and substantially flush against the mating edge surface of the other leaflet, with the plane of abutment being essentially the centerline plane of the valve body. The proportioning and the location of the slots 383 in the flat sidewall sections 385 of the valve body is such that, in the fully closed position, there is preferably contact between the right circular cylindrical wall of the peg 405 and the oblique sidewall 397c of the slot. The major part of the force of the blood against the outflow surface in the closed position is borne by the oblique flat surfaces 397c, and the angular orientation of these surfaces is adjusted so that tight mating contact is assured along the edge surfaces 413. The oblique surfaces 397c are preferably oriented at an angle so as to be within about 10° of parallel to the leaflet flat body sections in the closed position; for example if the leaflet lies at 45° to the centerline plane in the closed position, the surface 397c might lie at a downstream angle to the centerline plane of between about 35° and about 50°. However, the other factors discussed hereinbefore with respect to the heart valve 301 should be taken into consideration in determining the precise orientation to achieve the desired effect.

In the closed position, there may be little or essentially no leakage flow between the sidewall of the slot 383 lying farther from the centerline and the peg 405 because of the bearing contact with oblique sidewall section 397c. However, so that leakage flow along the base wall of the slots 383 and along the sidewall 397a, will not be greater than desired, as described hereinbefore, the location of the circular sector 415 (which remains on the end surface of the pegs after the size reduction) is oriented so that it provides a flowpath of desired length in this region as beet seen in FIG. 17. Moreover, the thickened side sections 399 are proportioned to likewise assure a flow path of appropriate length is present for controlled leakage which would begin in the slots 383 and then proceed between the flat wall sections 385 and the flat lateral edge surfaces 419 of the leaflets, thereby guarding against potentially too great a leakage flow at these locations.

When blood flow reverses, the downstream translation and the opening movement of the leaflets 401 in the valve 381 is essentially the same as that in the valve 301 described hereinbefore. One particular advantage of the construction of the valve 381 shown in FIGS. 13 through 19 is the avoidance of the need for maintaining close tolerances on the exterior surfaces of the thickened side sections 399 of the leaflets because the arcuate camming surfaces are not employed, and therefore manufacturing procedures are facilitated.

Shown in FIGS. 20 to 22 is an alternative embodiment of a heart valve 421 similar to that shown in FIGS. 13–19 which utilizes only a single valve member 423. The heart valve 421 has a valve body 425 which is generally annular in shape but contoured so as to have an upstream extension 427 and a downstream extension 429 as best seen in FIG. 20. The interior surface of the valve body is of right circular cylindrical construction except for a pair of diametrically opposed flat sections 431 where slots 433 generally similar to the slots 383 are located. A pair of diametrically opposed projections 435 also are provided in the flat sidewall regions for the purpose of providing camming surfaces 437 similar to the surfaces 391 of the valves 381.

A single valve member 423 generally in the form of a flat plate of uniform thickness is employed and proportioned to close the passageway through the valve body 425 when in the position depicted in FIG. 20. The valve member 423 has a pair of side sections 441 of increased thickness which support a pair of laterally extending right circular cylindrical pegs 443 similar to the pegs 405 that are received in the slots 433; the pegs are located eccentrically to the central plane of the flat plate. The valve member 423 has an essentially flat outflow surface 445 and a flat parallel inflow surface 447, with a pair of lugs 449 extending from the inflow surface 447 in the side sections; each lug has a rounded edge 451 that contacts a camming surface 437 of one projection in the open position, as best seen in FIG. 21. A curved upstream edge 453 of the valve member and a curved downstream edge 455 are both contoured so as to seal against the interior cylindrical surface 423 of the valve body in the closed position, as best seen in FIG. 20.

The construction and asymmetry of the slots 433 is substantially the same as that described with respect to the slots 383. As can be seen from FIG. 21, when in the full open position, the valve member 423 is oriented precisely parallel to the centerline 457 of the valve passageway, with the pegs 443 being located at the downstream ends of the enlarged central sections 461 of the slots. In this position, there is engagement between the curved edges 451 of the lugs 449 and the camming surfaces 437 of the projections, and there is engagement of each peg with the curved shoulder 463a on the side of the slot 443 farther away from the centerline. The curved shoulders 463a and 463b form the transition region to downstream slot extensions 465. During the duration of the period wherein the flow rate of blood through the valve passageway is high, the valve member assumes this orientation precisely parallel to the centerline and thus provides low resistance to blood flow through the passageway.

However, near the end of a pumping stroke of blood through the valve, for example, the rate of flow of blood slows, and the forces exerted by the blood rushing through the passageway are no longer predominant. As a result, the drag force of the downstream flowing blood becomes dominant, and the valve member 423 is displaced slightly farther downstream so that the peg 443 is now in contact with both of the curved downstream shoulders 463a and b, as depicted in FIG. 22. In moving to this ultimate position, the continued contact between the camming surface 437 and the curved edge 451 of the lug causes a slight rotation of the valve member 423 toward the eventual closed position orientation. Thus, as in the heart valve 381, the benefits of the precisely parallel orientation are obtained during the period of high flow rate of blood, yet pre-rotation of the valve member just prior to reverse flow is accomplished to advantageously position the valve member for preferential impingement of the backflowing blood against the outflow surface 445 which, as described above, accelerates the closing movement and reduces regurgitation. In essentially all other aspects, the guidance for the closing movement of the single valve member 423 is substantially the same as that described for each one of the leaflets in the heart valve 381.

Although the invention has been described with respect to certain preferred embodiments, which include what the inventors presently consider to be the best mode for carrying out the invention, it should be understood that various changes and modifications as would be obvious to one having the ordinary skill in this art may be made without departing from the scope of the invention which is defined by the claims appended hereto. For example, as earlier indicated, the invention is not limited to occluders in the form of valve members having flat body sections but is considered to be also applicable to valve members having curved main body sections; for example, it may be desirable to facilitate the creation of a central passageway of greater area through a bi-leaflet valve (compared to a similar valve having two flat leaflets) by using a pair of curved leaflets which may also achieve a more desirable flow pattern. As can be seen from FIGS. 20–22, the invention is also applicable to valves which employ a single occluder.

By camming contact in this application is meant contact wherein there is relative sliding movement along a surface which is inclined to the centerline plane through the valve body so as to cause a valve member to pivot toward its closed position. By a substantial distance as used herein, is meant a distance equal to or greater than the average thickness of the main body portion of the occluder.

Particular features of the invention are emphasized in the claims that follow.

What is claimed is:

1. A prosthetic heart valve which comprises
a generally annular valve body having an interior wall which defines a central passageway for blood flow therethrough, having a longitudinal axis,
occluder means having an inflow surface, an upstream edge and an outflow surface, said occluder means being mounted in said valve body to alternate between an open position, which permits flow of blood therethrough in a downstream direction generally parallel to said longitudinal axis, and a closed position, which blocks the flow of blood in the reverse direction, said inflow surface facing generally upstream and said outflow surface facing generally downstream with said occluder means in the closed position, and
a pivot arrangement by which said occluder means is guided in sliding-pivoting movement between said open position and said closed position,
said pivot arrangement including
projection means which extends generally radially inward from said valve body interior wall at an upstream location, said occluder means engaging said projection means in said open position and sliding upstream in sliding engagement thereagainst during an initial closing movement of said occluder means, and
interengaging elements on said valve body at a second location downstream of said upstream location and on said occluder means, which elements interengage and cooperate with said projection means in guiding the closing movement of said occluder means,
said sliding engagement between said projection means and said occluder means in combination with said contact between said interengaging elements, as said occluder means is being displaced upstream when reverse flow of blood begins through said central passageway, being such as to cause said occluder means to pivot toward said closed position,
said interengaging elements being in contact with each other at a first position when blood flow is near maximum flow through said passageway, in which position said outflow and inflow surfaces of said occluder means are oriented parallel to said longitudinal axis, and
said contact between said interengaging elements shifting downstream to a second position, which is downstream of said first position, when blood flow slows prior to reversing, and as a result of said downstream shifting, said occluder means pivots toward its closed position orientation.

2. A prosthetic heart valve according to claim 1 wherein said occluder means includes a pair of flat lateral surfaces parallel to each other which surfaces respectively lie in juxtaposition with two diametrically opposite flat wall sections formed in said interior wall of said annular valve body, and wherein said interengaging means includes depression means located in each said flat wall section and a pair of ear means each having an arcuate surface portion, each one of said ear means protruding laterally from each one of said flat lateral surfaces of said occluder means and one of said ear means being received in each said depression means.

3. A prosthetic heart valve according to claim 2 wherein each said ear means includes a right circular cylinder having a diameter greater than the length of said cylinder.

4. A prosthetic heart valve according to claim 3 wherein said depression means is in the form of a slot which is elongated in a direction generally parallel to said longitudinal axis of said valve body passageway and which has a central section of greater width than a pair of upstream and downstream end sections.

5. A prosthetic heart valve according to claim 4 wherein the width of said central section is greater than the diameter of said right circular cylinder of said ear means by about 10 percent or less, wherein said upstream and downstream end sections are of a width equal to between about 30 and about 60 percent of the width of said central section, and wherein said central section of said slot has a longitudinal dimension such that said ear means can travel a maximum distance in a straight-line direction equal to about 50 percent of the diameter of said right circular cylinder.

6. A prosthetic heart valve according to claim 2 wherein said projection means includes a flat surface which is engaged by an upstream edge potion of said occluder means inflow surface, said flat surface being oriented at an acute downstream angle of between about 5° and about 35° to a plane which is perpendicular to said flat wall sections of said valve body and which includes said longitudinal axis.

7. A prosthetic heart valve which comprises
a generally annular valve body having an interior, generally arcuate wall which defines a central passageway having a longitudinal axis for blood flow therethrough,
a pair of cooperating leaflets, each having an inflow surface, an outflow surface and a pair of opposite lateral edge surfaces, said leaflets being mounted in said valve body to alternate between an open position where flow of blood in a downstream direction is permitted and a closed position where flow of blood in a reverse direction is blocked, and
a pivot arrangement by which said leaflets are guided in moving between said open position and said closed position, said arrangement permitting said leaflets to assume an orientation substantially parallel to said longitudinal axis in their open position while said leaflets are axially displaceable upstream, relative to said valve body, upon the reversal of blood flow,
said pivot arrangement including
first interengaging means formed at an upstream location on said valve body and on said occluders, which first interengaging means exerts a camming action upon an upstream portion of each of said leaflets upon upstream axial displacement of said leaflets, which camming action is effective to cause each said leaflet to immediately begin to swing toward its closed position orientation, and
second interengaging means on said valve body, at a location downstream of said upstream location, and on each said leaflet adjacent each lateral edge surfacer thereof,
contact at said second interengaging means between said valve body and each said leaflet being such as to cause said leaflets to assume an open position orientation in which said inflow and outflow surfaces are substantially parallel to said longitudinal axis when blood flows at near maximum flow rate and being such as to cause each said leaflet to shift to a downstream position when the blood flow slows prior to reversing, as a result of which downstream shifting, each of said leaflets rotates up to about 5° toward its closed position orientation and is no longer parallel to said longitudinal axis.

8. A prosthetic heart valve according to claim 7 wherein said second interengaging means includes depression means in said valve body sidewall and ear means laterally protruding from said opposite lateral edge surfaces of each said leaflet, which ear means is received in said depression means.

9. A prosthetic heart valve according to claim 8 wherein said depression means includes open-ended slots which have centerlines parallel to said valve body longitudinal axis and which have central sections that are asymmetric about said centerlines.

10. A prosthetic heart valve which comprises
an annular valve body having an interior wall which defines a passageway therethrough for flow of blood in a downstream direction, which passageway has a longitudinal axis,
a pair of leaflets which translate and pivot to alternatively open and close said passageway to flow of blood therethrough,
each of said leaflets having a main body portion with an upstream edge and a pair of coaxial, oppositely extending lateral ears,
each said ear having a generally circular cylindrical bearing surface,
said annular valve body interior wall having a pair of diametrically opposed flat wall sections, each of said flat wall sections having formed therein a pair of depressions for respectively receiving one said ear of each of said leaflets,
each said depression including a central section having a first flat sidewall portion which is perpendicular to said flat wall section of said valve body and generally parallel to said longitudinal axis of said central passageway of said valve body,
said first flat sidewall potion of each depression means facing away from a centerline plane which includes said valve body longitudinal axis and is perpendicular to said valve body flat wall sections,
said valve body also having a plurality of projections which at least in part protrude generally radially inward from said flat wall sections, each of said projections having a camming surface,
said projections being located upstream of portions of said depressions so that said camming surfaces are engaged by said leaflets at locations generally along said upstream edges of said leaflets when said leaflets are located in the open position, and said depressions being located so that said leaflets assume an orientation wherein said main body portion of each said leaflet is aligned parallel with said longitudinal axis when blood flow is near a maximum flow and so that said leaflets shift to a downstream position when blood flow slows prior to reversing, during which downstream shifting said leaflets pivot slightly toward their closed position orientations.

11. A heart valve according to claim 10 wherein each said camming surface is a flat surface that faces said centerline plane and is aligned at a downstream angle of between about 5° and about 35° to said centerline plane.

12. A heart valve according to claim 11 wherein each said depression is a slot having a longitudinal centerline that is defined by centers of a pair of aligned upstream and downstream elongated terminal sections which flank said wider central section, wherein said central section of said slot has an opposite second flat sidewall portion which is spaced from and substantially parallel to said first flat sidewall portion, wherein each of said elongated terminal sections has a width less than a spacing between said parallel first and second sidewall portions, and wherein said slot also has upstream and downstream curved transition sections located between said central section and each respective terminal section.

13. A heart valve according to claim 12 wherein each said ear includes a right circular cylindrical element having a diameter greater than said width of said terminal sections of said slot and at least about 90 percent of said spacing between said first and second parallel sidewall portions.

14. A heart valve according to claim 13 wherein engagement between the upstream region of each central section and said respective right circular cylindrical ear assists in guiding the movement of said leaflets as each leaflet pivots to close said passageway.

15. A heart valve according to claim 14 wherein said first and second flat sidewall sections of each said slot are parallel to said centerline through said slot and wherein said second flat sidewall section is spaced further away from said slot axial centerline than is said first flat sidewall section.

16. A heart valve according to claim 15 wherein, in the open position, there is engagement between each said ear and only one of said downstream curved transition sections of said slots when said blood flow is near its maximum flow rate.

17. A heart valve according to claim 16 wherein there is engagement between each said ear and both of said downstream curved transition sections following said downstream shifting.

* * * * *

UNITED STATES PATENT AND TRADEMARK OFFICE
CERTIFICATE OF CORRECTION

PATENT NO. : 5,350,421
DATED : September 27, 1994
INVENTOR(S) : Stupka, et al

It is certified that error appears in the above-indentified patent and that said Letters Patent is hereby corrected as shown below:

Column 18, Claim 6, line 24, correct the spelling of --portion--; Column 18, Claim 7, line 62, change "surfacer" to --surface--; Column 19, Claim 10, line 23-24, change "alternatively" to --alternately--; Column 19, Claim 10, line 41, correct the spelling of --portion--.

Signed and Sealed this

Twenty-seventh Day of December, 1994

Attest:

BRUCE LEHMAN

*Attesting Officer*      *Commissioner of Patents and Trademarks*